United States Patent
Park et al.

(10) Patent No.: US 10,215,697 B2
(45) Date of Patent: Feb. 26, 2019

(54) METHOD AND APPARATUS FOR MEASURING 3D REFRACTIVE-INDEX TOMOGRAMS USING HIGH-SPEED WAVEFRONT SHAPER

(71) Applicant: Korea Advanced Institute of Science and Technology, Daejeon (KR)

(72) Inventors: YongKeun Park, Daejeon (KR); Kyoohyun Kim, Suwon-si (KR); Seungwoo Shin, Busan (KR)

(73) Assignee: TOMOCUBE, INC., Daejeon (KR)

( * ) Notice: Subject to any disclaimer, the term of this patent is extended or adjusted under 35 U.S.C. 154(b) by 135 days.

(21) Appl. No.: 14/981,355

(22) Filed: Dec. 28, 2015

(65) Prior Publication Data
US 2017/0023471 A1     Jan. 26, 2017

(30) Foreign Application Priority Data

Jul. 20, 2015  (KR) .................. 10-2015-0102417

(51) Int. Cl.
  *G01N 21/45*  (2006.01)
(52) U.S. Cl.
  CPC ........... *G01N 21/45* (2013.01); *G01N 21/453* (2013.01); *G01N 2201/068* (2013.01)
(58) Field of Classification Search
  CPC .... G01N 21/45; G01N 23/046; G01N 21/453; G01N 2201/068; G01B 9/02091
  See application file for complete search history.

(56) References Cited

U.S. PATENT DOCUMENTS

| 2006/0058682 | A1* | 3/2006 | Miller | A61B 3/102 600/476 |
| 2007/0263226 | A1* | 11/2007 | Kurtz | A61B 5/0059 356/492 |
| 2012/0182561 | A1* | 7/2012 | Masumura | A61B 5/0095 356/601 |
| 2014/0055789 | A1* | 2/2014 | Lim | G01B 9/02091 356/479 |
| 2014/0146324 | A1* | 5/2014 | Lim | G01B 9/02038 356/497 |

(Continued)

FOREIGN PATENT DOCUMENTS

| JP | 2001-507258 A | 6/2001 |
| JP | 2005-506107 | 3/2005 |

(Continued)

OTHER PUBLICATIONS

Office Action for Japanese Patent Application No. JP 2015-247292, dated Jan. 4, 2017, 8 Pages.

(Continued)

*Primary Examiner* — Michael P LaPage
(74) *Attorney, Agent, or Firm* — Fenwick & West LLP (57) ABSTRACT

A method and apparatus for measuring 3D refractive-index tomograms using a wavefront shaper in ultra-high speed and high precision is provided. The method includes the steps of modifying at least one of an illumination angle and a wavefront pattern of an incident ray through the wavefront shaper and leading the modified incident ray to a sample, measuring a 2D optical field, which passes through the sample, through an interferometry along at least one or more of the incident rays, and obtaining 3D refractive-index tomograms through measured information of the 2D optical field.

2 Claims, 6 Drawing Sheets

(56) References Cited

U.S. PATENT DOCUMENTS

| | | | | |
|---|---|---|---|---|
| 2014/0252200 | A1* | 9/2014 | Garsha | G02B 21/367 250/201.3 |
| 2015/0131104 | A1* | 5/2015 | Lim | G01B 9/02083 356/479 |
| 2017/0105618 | A1* | 4/2017 | Schmoll | A61B 3/102 |
| 2017/0211924 | A1* | 7/2017 | Vogler | G01B 9/02091 |

FOREIGN PATENT DOCUMENTS

| | | |
|---|---|---|
| JP | 2009-500856 | 1/2009 |
| JP | 4725967 B2 | 7/2011 |
| JP | 2011-527218 | 10/2011 |
| JP | 2014-097430 | 5/2014 |
| JP | 2014-104362 | 6/2014 |
| JP | 2014-530362 | 11/2014 |
| JP | 2014-228425 | 12/2014 |
| JP | 2015-519604 A | 7/2015 |
| KR | 10-1352803 B1 | 1/2014 |
| WO | WO 03027749 A2 | 4/2003 |

OTHER PUBLICATIONS

Goorden, a., et al., "Superpixel-based spatial amplitude and phase modulation using a digital micromirror device," Optics Express, Jul. 28, 2014, pp. 17999-18009, vol. 22, No. 15.

Fercher, A.F., et al., "Image formation by inversion of scattered field data: experiments and computational simulation," Applied Optics, Jul. 15, 1979, pp. 2427-2439, vol. 18, No. 14.

Kim, K., et al., "High-resolution three-dimensional imaging of red blood cells parasitized by Plasmodium falciparum and in situ hemozoin crystals using optical diffraction tomography," Journal of Biomedical Optics, Jan. 2014, pp. 011005-1-011005-12, vol. 19, No. 1.

Lee, K., et al., "Quantitative Phase Imaging Techniques for the Study of Cell Pathophysiology: From Principles to Applications," Sensors, 2013, pp. 4170-4191, vol. 13.

Lee, W.-H., "Binary computer-generated holograms," Applied Optics, Nov. 1, 1979, pp. 3661-3669, vol. 18, No. 21.

Shin, S., et al., "Active illumination using a digital micromirror device for quantitative phase imaging," Cornell University Library, Jun. 20, 2015, 7 pages, Can be retrieved at <URL:http://arxiv.org/abs/1506.06237>.

Wolf, E., "Three-Dimensional Structure Determination of Semi-Transparent Objects From Holographic Data," Optics Communications, Sep./Oct. 1969, pp. 153-156, vol. 1, No. 4.

Korean Office Action, Korean Application No. 10-2016-0103632, dated Aug. 29, 2016, 7 pages (with concise explanation of relevance).

* cited by examiner

METHOD AND APPARATUS FOR MEASURING 3D REFRACTIVE-INDEX TOMOGRAMS USING HIGH-SPEED WAVEFRONT SHAPER

CROSS-REFERENCE TO RELATED APPLICATION(S)

This application claims the benefit under 35 U.S.C. § 119(a) of a Korean patent application filed on Jul. 20, 2015 in the Korean Intellectual Property Office and assigned Serial number 10-2015-0102417, the entire disclosure of which is hereby incorporated by reference in its entirety.

TECHNICAL FIELD

Embodiments of the present disclosure relate to a method and apparatus for measuring 3D refractive-index tomograms using a wavefront shaper in ultra-high speed and high precision. More particularly, embodiments of the present disclosure relate to a method and apparatus for measuring 3D refractive-index tomograms using a wavefront shaper, in ultra-high speed and high precision, to control incident rays in optical tomography.

BACKGROUND

A 3D Refractive-Index Tomography (RIT), as a kind of optical technology which is proposed by E. Wolf and practiced by A. F. Fercher et al., may be employed in measuring optical characteristics and specimen (sample) patterns through measurement of 3D refractive-index distribution for semiconductor fabrication products or microscopic specimens (samples) such as cells [Non-patent documents 1 to 3]. The RIT may implement X-ray Computer Tomography (CT) by optics, by which a multiplicity of sheets of 2D holographic images (including optical absorption images and optical phase retardation images) is taken by changing general incident angles of plane waves on a sample and a 3D scattering potential is calculated from the multiplicity of 2D holographic images.

Conventionally, changing angles of plane waves is carried out by a galvanometer mirror [Non-patent document 2], or by a Liquid Crystal-based Spatial Light Modulator (LC-SLM).

However, those ways have some problems with speed and accuracy in measurement. For example, in a mode of directly rotating a sample, it has been difficult to fix a pivot of the sample and could be affected from vibration. Furthermore, if biological samples such as cells are directly rotating, there would be deformation of the samples.

In the case of employing a galvanometer mirror, it has been difficult to stably control incident angles due to microscopic vibrations and has not been allowable to complete exact optical alignment because of disagreement between a reflective surface and a pivot of the galvanometer mirror. Moreover, a LC-SLM is basically incapable of performing high-speed tomography due to a limit to response speed of liquid crystals, and very expensive to cause an increase of a unit product cost.

PRIOR ART DOCUMENTS

Non-Patent

1. E. Wolf, "Three-dimensional structure determination of semi-transparent objects from holographic data," Optics Communications 1, 153-156 (1969).
2. A. F. Fercher, et al., "Image formation by inversion of scattered field data: experiments and computational simulation," Applied Optics 18(14), 2427-2439 (1979).
3. K. Kim, H.-O. Yoon, M. Diez-Silva, M. Dao, R. Dasari, and Y.-K. Park, "High-resolution three-dimensional imaging of red blood cells parasitized by Plasmodium falciparum and in situ hemozoin crystals using optical diffraction tomography," J. Biomed. Opt. 19, 011005-011012 (2014).
4. W.-H. Lee, "Binary computer-generated holograms," Applied Optics 18, 3661-3669 (1979).
5. S. A. Goorden, J. Bertolotti, and A. P. Mosk, "Superpixel-based spatial amplitude and phase modulation using a digital micromirror device," Optics express 22, 17999-18009 (2014).
6. K. Lee, K. Kim, J. Jung, J. Heo, S. Cho, S. Lee, G Chang, Y. Jo, H. Park, and Y. Park, "Quantitative phase imaging techniques for the study of cell pathophysiology: from principles to applications," Sensors 13, 4170-4191 (2013).

SUMMARY

Aspects of the present disclosure are to address at least the above-mentioned problems and/or disadvantages and to provide at least the advantages described below. Accordingly, embodiments of the present disclosure are to provide a method and apparatus for measuring 3D refractive-index tomograms using a wavefront shaper in ultra-high speed and high precision, more particularly, to provide a method and apparatus for measuring 3D refractive-index tomograms using a wavefront shaper, in ultra-high speed and high precision, to control incident rays in optical tomography.

In another aspect, embodiments of the present disclosure are to provide a method and apparatus for measuring 3D refractive-index tomograms using a wavefront shaper, in high speed and precision, by controlling incident rays to have different angles or patterns for ultra-high speed tomography and by controlling incident rays stably and fast.

In accordance with an aspect of the present disclosure, a method for measuring 3D refractive-index tomograms using a wavefront shaper in ultra-high speed and high precision may include the steps of modifying at least one of an illumination angle and a wavefront pattern of an incident ray through the wavefront shaper and leading the modified incident ray to a sample, measuring a 2D optical field, which passes through the sample, through an interferometer along at least one or more of the incident rays, and obtaining 3D refractive-index tomograms through measured information of the 2D optical field.

In an embodiment, the step of leading the modified incident ray to the sample may include the steps of using the wavefront shaper as a deformable mirror (DM) and controlling an inclining angle of the DM to control a plane-wave advancing angle of the incident ray; and enlarging the controlled plane-wave advancing angle through a plurality of lenses and leading the enlarged incident ray to the sample.

The step of controlling the plane-wave advancing angle may include the step of controlling the plane-wave advancing angle to be two times of a gradient shown in the DM.

The step of leading the modified incident ray to the sample may include the steps of using a digital micromirror device (DMD), which has an array including a multiplicity of micromirrors, as the wavefront shaper and interposing a spatial filter between a first lens and a second lens that transmit the second optical field reflected from the DMD; controlling a plane-wave advancing angle of the incident ray that has a linear gradient by controlling a phase of a first diffracted ray passing through the spatial filter; and enlarging the controlled plane-wave advancing angle and leading the enlarged incident ray to the sample.

The step of leading of the modified incident ray to the sample may include the steps of using a digital micromirror device (DMD), which has an array including a multiplicity of micromirrors, as the wavefront shaper and aligning at least one or more centers of a first lens and a second lens, which transmit the 2D optical field reflected from the DMD, to stray by a specific interval from an optical axis; interposing a spatial filter between the first lens and the second lens, treating pixels of the DMD, which are grouped to compose a superpixel, as to such a degree that the pixels are hardly distinctive by scaling-down the spatial filter to a diffraction limit, and forming a superpixel array whose phase is adjustable in the range of 0~2π; adjusting the phase of the superpixel and controlling a plane-wave advancing angle of the incident ray having a linear phase gradient; and enlarging the controlled plane-wave advancing angle through a plurality of lenses and leading the enlarged incident ray to the sample.

The step of leading the modified incident ray to the sample may include the steps of using a digital micromirror device (DMD), which has an array including a multiplicity of micromirrors, as the wavefront shaper, placing the DMD on an optically aligned Fourier plane, and forming a laser array that is controllable with positions of the multiplicity of micromirrors by individual light sources; changing the positions of the multiplicity of micromirrors that reflects the incident ray through the laser array and controlling a plane-wave advancing angle of the incident angle; and enlarging the controlled plane-wave advancing angle through a plurality of lenses and leading the enlarged incident ray to the sample.

The step of obtaining the 3D refractive-index tomograms may include the step of obtaining 3D scattering potentials or the 3D refractive-index tomograms in a 3D optical diffraction tomography algorithm.

In another embodiment, a method for measuring 3D refractive-index tomograms using a wavefront shaper in ultra-high speed and high precision may include the steps of using a digital micromirror device (DMD) and leading at least one or more incident ray patterns to a surface of a sample; modifying the incident ray pattern and measuring a 2D optical field to the at least one or more incident ray patterns through an interferometer; and numerically analyzing a reaction of the sample to differently angled plane waves, which are included in the incident pattern, from the measured 2D optical field.

In accordance with another aspect of the present disclosure, an apparatus for measuring 3D refractive-index tomograms using a wavefront shaper in ultra-high speed and high precision may include a modulation part configured to modify at least one of an illumination angle and a wavefront pattern of an incident ray through the wavefront shaper and to lead the modified incident ray to a sample; an interferometer configured to measure a 2D optical field, which passes through the sample, along at least one or more of the incident rays; and an imaging part configured to obtain 3D refractive-index tomograms through information of the measured 2D optical field.

The modulation part may include a deformable mirror (DM) used as the wavefront shaper and configured to control a plane-wave advancing angle of the incident ray by controlling an inclining angle; and a plurality of lenses configured to enlarge the plane-wave advancing angle and to lead the enlarged incident ray to the sample.

The modulation part may include a digital micromirror device (DMD) used as the wavefront shaper with an array including a multiplicity of micromirrors; a first lens and a second lens that transmit the 2D optical field that is reflected from the DMD; a spatial filter interposed between the first lens and the second lens, and configured to adjust a phase of a first diffracted ray and to control a plane-wave advancing angle of the incident ray having a linear gradient; and a plurality of lenses configured to enlarge the plane-wave advancing angle and to lead the enlarged incident ray to the sample.

The modulation part may include a digital micromirror device (DMD) used as the wavefront shaper with an array including a multiplicity of micromirrors; a first lens and a second lens that transmit the 2D optical field that is reflected from the DMD, at least one or more centers of the lenses being aligned to stray by a specific interval from an optical axis; a spatial filter interposed between the first lens and the second lens; and a plurality of lenses configured to enlarge the plane-wave advancing angle of the incident angle and to lead the enlarged incident ray to the sample, wherein the modulation part may treat pixels of the DMD, which are grouped to compose a superpixel, as to such a degree that the pixels are hardly distinctive by scaling-down the spatial filter to a diffraction limit, may form a superpixel array whose phase is adjustable in the range of 0~2π, adjusts the phase of the superpixel, and may control the plane-wave advancing angle of the incident ray having a linear phase gradient.

The modulation part may include a digital micromirror device (DMD) used as the wavefront shaper with an array including a multiplicity of micromirrors; a first lens configured to transmit the 2D optical field that is reflected from the DMD; and a plurality of lenses configured to enlarge the plane-wave advancing angle of the incident angle and to lead the enlarged incident ray to the sample, wherein the modulation part may place the DMD on an optically aligned Fourier plane, may form a laser array that is controllable with positions of the multiplicity of micromirrors by individual light sources, may change the positions of the multiplicity of micromirrors that reflects the incident ray through the laser array, and may control the plane-wave advancing angle of the incident angle.

The imaging part may obtain 3D scattering potentials or the 3D refractive-index tomograms in a 3D optical diffraction tomography algorithm.

In accordance with still another aspect of the present disclosure, an apparatus for measuring 3D refractive-index tomograms using a wavefront shaper in ultra-high speed and high precision may include a digital micromirror device (DMD) configured to lead at least one or more incident ray patterns to a surface of a sample; a first lens and a second lens that enlarge a plane-wave advancing angle of the incident ray and lead the enlarged incident ray to the sample; an interferometer configured to modify the incident ray pattern and to measure a 2D optical field to the incident ray pattern; and an imaging part configured to numerically analyze a reaction of the sample to differently angled plane waves, which are included in the incident pattern, from information of the measured 2D optical field and to obtain 3D refractive-index tomograms.

According to embodiments of the present disclosure, it may be accomplishable to provide a method and apparatus for measuring 3D refractive-index tomograms using a wavefront shaper, in high speed and precision, by controlling incident rays to have different angles or patterns for ultra-high speed tomography and by controlling incident rays stably and fast.

According to embodiments of the present disclosure, it may be allowable to measure 3D refractive-index tomograms, in high speed and precision, with more stable and fast than a general galvanometer mirror, a mechanical specimen, or a light source in motion through ultra-high speed control for incident rays using a Deformable Mirror (DM) or a Digital Micromirror Device (DMD).

DETAILED DESCRIPTION

Hereinafter, various embodiments of the present disclosure will be described in conjunction with the accompanying drawings. Various embodiments described herein, however, may not be intentionally confined in specific embodiments, but should be construed as including diverse modifications, equivalents, and/or alternatives. Throughout the descriptions of the drawings, like reference numerals refer to like elements. In the drawings, patterns and sizes of elements may be exaggerated in view of apparent illustration and understanding.

Embodiments of the present disclosure are concerned with the technology of controlling incident rays for optical tomography using a wavefront shaper, more specifically with the technology of controlling incident rays to have different angles or patterns for optical tomography in stability and high speed. A device capable of controlling a wavefront in ultra-high speed may include a DM or DMD.

The technology employing such devices may be operable with several methods according to optical alignment therein. The following embodiments will be described on the technology for controlling incident rays using a DM and a DMD.

Figure 1:
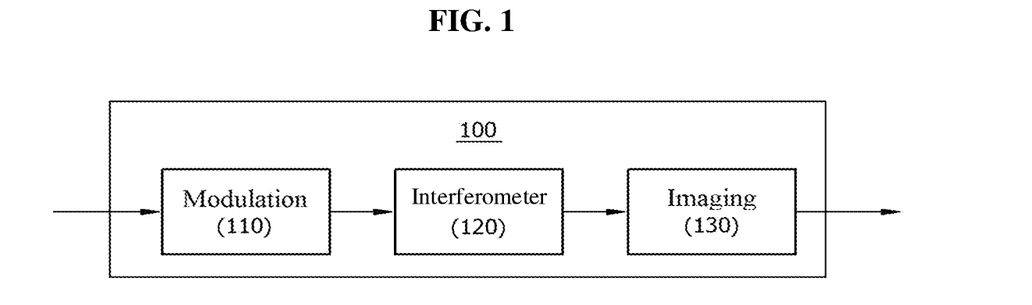
FIG. 1 is a schematic block diagram illustrating an ultra-high speed/high-precision 3D refractive-index measuring apparatus using a wavefront shaper according to an embodiment of the present disclosure.

FIG. 1 is a schematic block diagram illustrating an ultra-high speed/high-precision 3D refractive-index measuring apparatus using a wavefront shaper according to an embodiment of the present disclosure.

Referring to FIG. 1, an ultra-high speed/high-precision 3D refractive-index measuring apparatus 100 using a wavefront shaper may be configured to include a modulation part 110, an interferometer 120, and an imaging part 130.

The modulation part 110 may modify at least one of an illumination angle and a wavefront pattern of an incident ray, using a wavefront shaper, and may lead the modified incident ray to a sample (specimen). A wavefront shaper may be formed with a device capable of a phase of light or a film of fixed type capable of controlling a phase of light. For example, a wavefront shaper may include a DM or DMD capable of controlling a wavefront in ultra-high speed.

The interferometer 120 may measure a 2D optical field, which pass through a sample, along at least one or more of incident rays by extracting an interference signal from at least one or more of incident rays.

The imaging part 130 may obtain 3D refractive-index tomograms through information of a measured 2D optical field, hence providing an ultra-high/high-precision 3D refractive-index measuring method and apparatus using a wavefront shaper capable of measuring 3D refractive-index tomograms in high speed and precision.

Hereinafter, the technology for measuring 3D refractive-index tomograms, in ultra-high speed and high precision, using a wavefront shaper through embodiments of the present disclosure.

Figure 2:
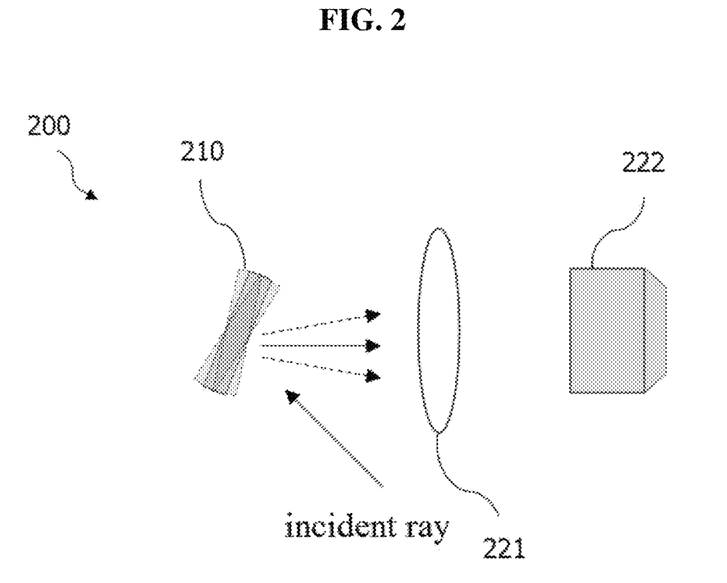
FIG. 2 is a diagram illustrating an ultra-high speed/high-precision 3D refractive-index measuring apparatus using a deformable mirror according to an embodiment of the present disclosure.

FIG. 2 is a diagram illustrating an ultra-high speed/high-precision 3D refractive-index measuring apparatus using a deformable mirror (DM) according to an embodiment of the present disclosure.

Referring to FIG. 2, it may be allowable to directly control an inclining angle of a DM for controlling an advancing angle of a plane wave.

An ultra-high speed/high-precision 3D refractive-index measuring apparatus 200 using a DM may be formed to include a modulation part, an interferometer, and an imaging part.

The modulation part may modify at least one of an illumination angle and a wavefront pattern of an incident ray through a wavefront shaper and may lead the modified incident ray to a sample.

In more detail, the modulation part may include a DM 210 and a plurality of lenses 221 and 222.

The DM 210, as a kind of wavefront shaper, may control an inclining angle of an incident ray to adjust a plane-wave advancing angle of the incident ray.

The plurality of lenses 221 and 222 may lead an incident ray, which is enlarged in plane-wave advancing angle, to a sample.

The DM 210 may be inclined by an angle to directly control a plan-wave advancing angle of an incident ray. During this, as a ray reflected from the DM 210 is incident on a sample, it may be allowable to control a plane-wave advancing angle in two times of a gradient of the DM 210. A ray with such a controlled plane-wave advancing angle may be enlarged by the plurality of lenses 221 and 222 and then may be incident on a sample, and thereby it may be permissible to measure a 2D optical field corresponding to the ray. The plurality of lenses 221 and 222 may be used as a tube lens 221 and a condenser lens 222, respectively.

The interferometer, for extracting an interference signal from at least one or more incident rays, may measure a 2D optical field, which passes through a sample, along at least one or more incident rays.

The imaging part may obtain 3D refractive-index tomograms through information of a measured 2D optical field. As such, the DM 210 may be inclined by angle to directly control a plane-wave advancing angle of an incident ray.

With respect to an operating sequence along a ray advancing course, a ray emitted from a light source may be controlled in phase by a wavefront shaper. The light source may include a light source of visible frequency range.

A wavefront shaper may be used to modify at least one of an illumination angle and a wavefront pattern of an incident ray which is led to a sample. The wavefront shaper may be used with the DM 210. By control an inclining angle of the DM 210, it may be allowable to control a plane-wave advancing angle of an incident ray, to enlarge the controlled plane-wave advancing angle through the plurality of lenses 221 and 222, and then to lead the incident ray with the enlarged plane-wave advancing angle to a sample. As a ray reflected from the DM 210 is led to a sample, it may be allowable to control a plane-wave advancing angle in two times of a gradient of the DM 210.

Then, by taking images of a 2D optical field, which passes through a sample, by the interferometer according respectively to at least one or more incident rays, it may be allowable to obtain 3D refractive-index tomograms through information of the measured 2D optical field.

Consequently, for ultra-high speed optical tomography, it may be allowable to measure 3D refractive-index tomograms in high speed and precision by controlling incident rays in stability and high speed, i.e., by controlling an inclining angle of the DM 210 to have incident rays different in plane-wave advancing angles each other.

Figure 3:
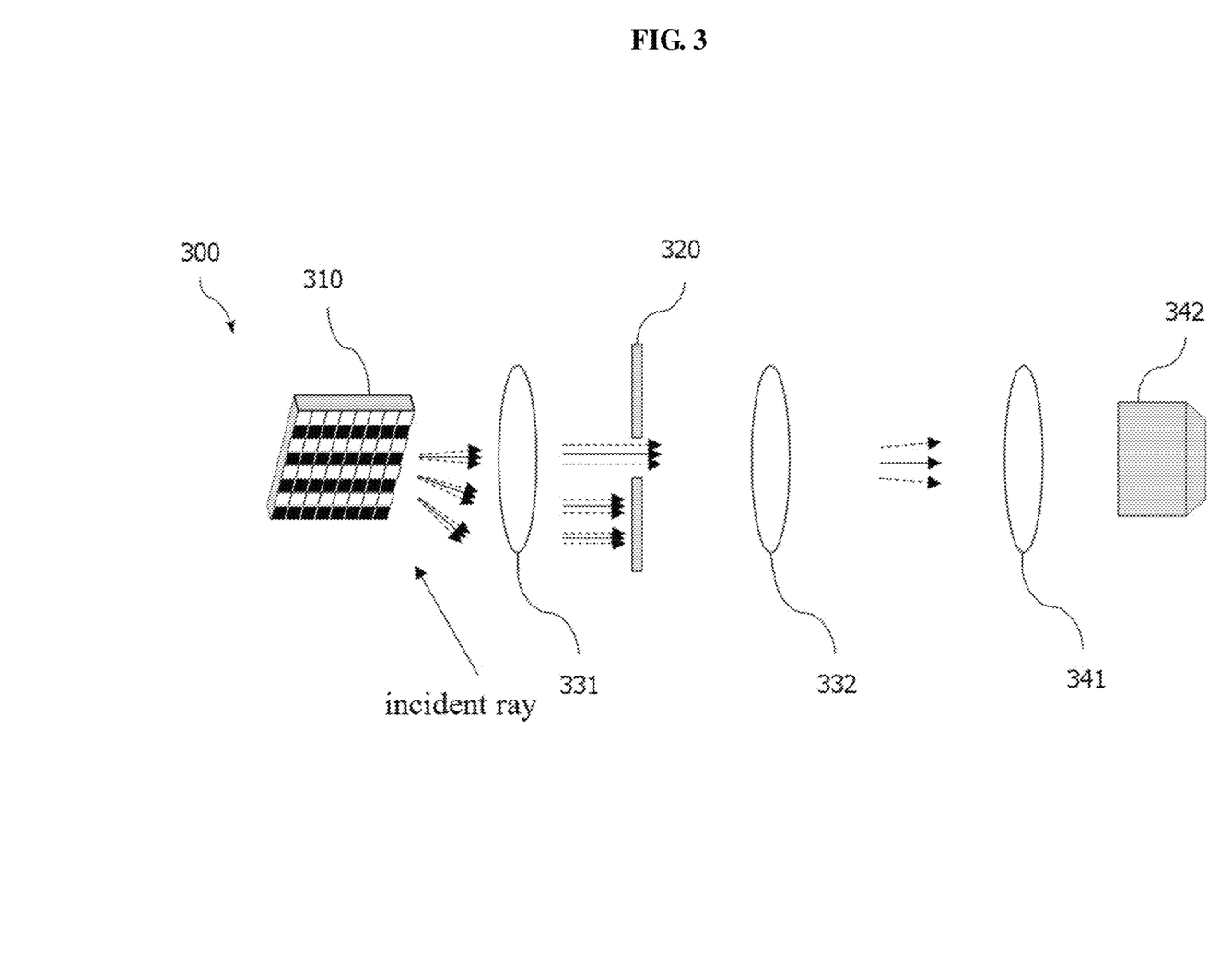
FIG. 3 is a diagram illustrating an ultra-high speed/high-precision 3D refractive-index measuring apparatus using a digital micromirror device according to another embodiment of the present disclosure.

FIG. 3 is a diagram illustrating an ultra-high speed/high-precision 3D refractive-index measuring apparatus using a digital micromirror device (DMD) according to another embodiment of the present disclosure.

Referring to FIG. 3, a DMD may be used as a period-controllable reflective amplitude grating.

An ultra-high speed/high-definition 3D refractive-index measuring apparatus using a DMD may be formed to include a modulation part, an interferometer, and an imaging part. In this configuration, the DMD may be used as a period-controllable reflective amplitude grating.

The modulation part may modify an illumination angle of an incident angle, which is led to a sample, through a wavefront shaper.

Additionally, the modulation part may include a DMD 310, a first lens 331, a second lens 332, a spatial filter 320, and a plurality of lenses 341 and 342. The plurality of lenses 341 and 342 may be used with, e.g., a tube lens and a condenser lens, respectively.

The DMD 310 may act as a wavefront shaper and may include an array including a multiplicity of micromirrors.

The first lens 331 and the second lens 332 may transmit a 2D optical field which is reflected from the DMD 310.

The spatial filter 320 may be interposed between the first lens 331 and the second lens 332 and may thereby adjust a phase of a first diffracted ray to control a plane-wave advancing angle of an incident ray having a linear gradient.

The plurality of lenses 341 and 342 may enlarge a plane-wave advancing angle of an incident ray which is led to a sample.

The interferometer may measure a 2D optical field, which passes through a sample, along at least one or more incident rays.

The imaging part may obtain 3D refractive-index tomograms through information of the measured 2D optical field.

In detail, it may be permissible to select phase information, which is desired for the first diffracted ray passing through the spatial filter 320, using the mechanism proposed by Lee hologram [Non-patent document 4] and to represent a plane wave, which advances in a desired angle, by preparing a phase of the plane wave with a linear gradient. To represent a plane wave advancing in a desired angle, it needs to provide a phase which spatially increases in linearity. While the DMD 310 may control only the intensity of a ray immediately after reflection, the Lee hologram including a phase to be represented may be represented in intensity of a ray. Accordingly, the DMD 310 may be used to represent a phase corresponding to a plane wave. In detail, assuming that an optical axis is assigned to the Z-axis and angles of the X- and Y-axes directions of a laser plane wave having a wavelength λ to be represented are denoted respectively by $\theta_x$ and $\theta_y$, a wavefront phase information φ(x, y) may given by Equation 1.

$$\phi(x,y)=(2\pi/\lambda)\{(\sin \theta_x)x/+(\sin \theta_y)y\} \quad \text{[Equation 1]}$$

To form a ray with such a wavefront through the DMD 310, it may be permissible to generate a hologram pattern as given by Equation 2.

$$f(x, y) = \frac{1}{2}[1 + \cos\{2\pi ux + 2\pi vy + \phi(x, y)\}] \quad \text{[Equation 2]}$$
$$= \frac{1}{2} + \frac{1}{4}\exp[j2\pi(ux + vy)]\exp[j\phi(x, y)] +$$
$$\frac{1}{4}\exp[-j2\pi(ux + vy)]\exp[-j\phi(x, y)].$$

In Equation 2, if a reflected ray corresponding to the second term is illuminated but other rays are shielded, the ray illuminated to the sample may be directly controlled with φ(x, y) on the DMD 310 to form a plane wave in a desired direction. During this, an undesired diffracted ray generated by using the hologram may be removed through the spatial filter 320.

Since a phase of each pixel can be controlled in the range 0~2π, a gradient of a phase controllable by the DMD 310 may be limited by a size of the pixel. Generally, if the DMD 310 is fabricated with micromirrors in several micrometers, the controllable maximum angle may be ranged in about 1~2 degrees. If a 2D optical field information is taken by angles of incident rays after enlarging the angle by adding two lenses, it may be allowable to obtain a 3D scattering potential.

With respect to an operating sequence along an advancing course of a ray, a ray emitted from a light source, like a laser, may be controlled with phase through a wavefront shaper. The light source may include a light source of visible frequency light range.

A wavefront shaper may be used to modify at least one of an illumination angle and a wavefront pattern of an incident ray which is led to a sample. The wavefront shaper may be used with the DMD 310 including an array with a multiplicity of micromirrors. The spatial filter 330 may be interposed between the first lens 331 and the second lens 332 which transmit a 2D optical field reflected from the DMD 310. A first diffracted ray passing through the spatial filter 320 may be adjusted in phase to control a plane-wave advancing angle of an incident ray having a linear gradient. Then, the controlled plane-wave advancing angle may be enlarged through the plurality of lenses 341 and 342 and the incident ray with the enlarged plane-wave advancing angle may be led to a sample.

A 2D optical field passing through a sample may be measured by the interferometer along at least one or more incident rays.

Then, it may be allowable to obtain 3D refractive-index tomograms through information of the measured 2D optical field.

Consequently, for ultra-high speed optical tomography, it may be allowable to measure 3D refractive-index tomograms in high speed and precision by using the DMD 310 for period-controllable reflective amplitude gratings to have incident rays different in angles each other and to control the incident rays in stability and high speed.

Figure 4:
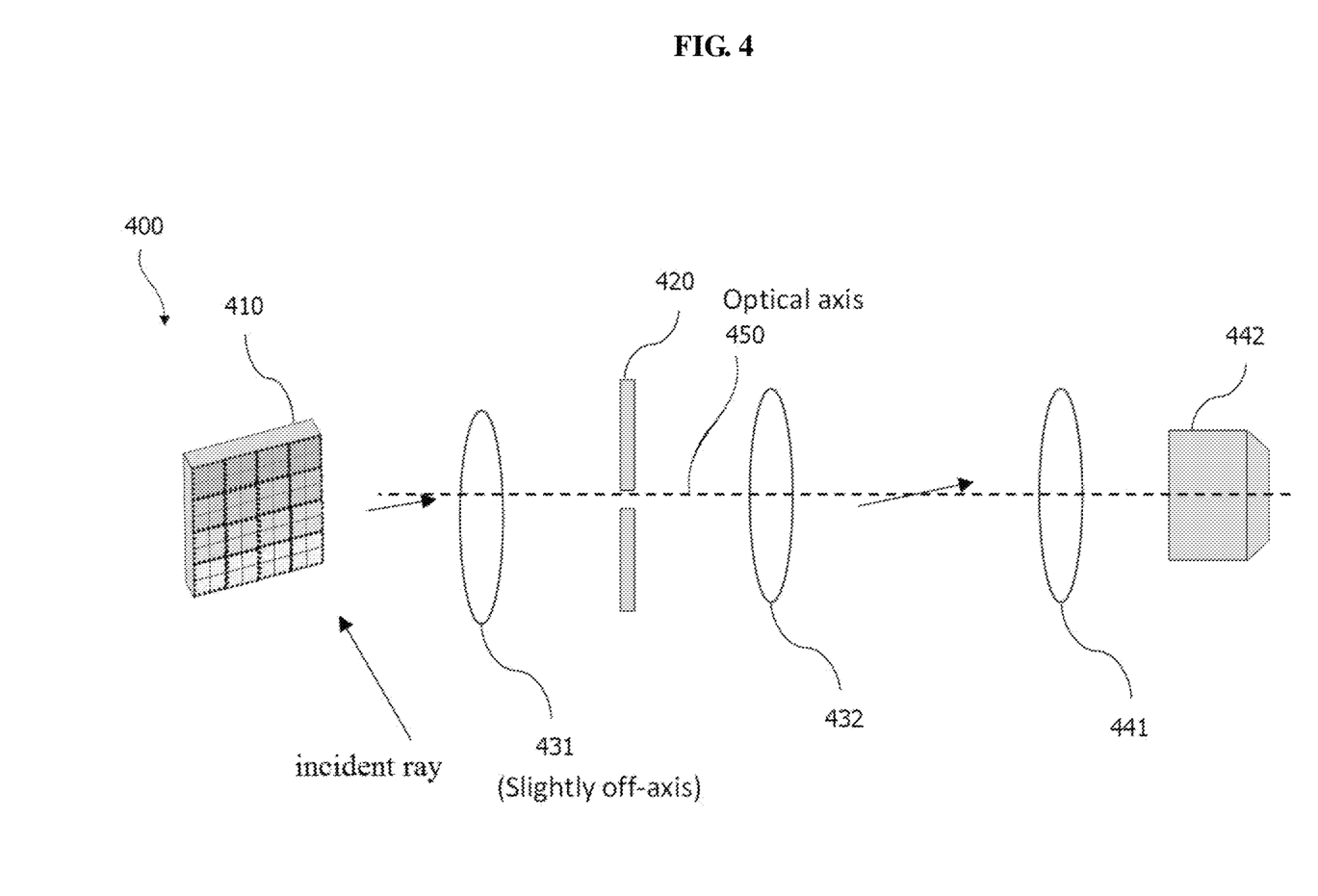
FIG. 4 is a diagram illustrating an ultra-high speed/high-precision 3D refractive-index measuring apparatus using a digital micromirror device according to still another embodiment of the present disclosure.

FIG. 4 is a diagram illustrating an ultra-high speed/high-precision 3D refractive-index measuring apparatus using a digital micromirror device (DMD) according to still another embodiment of the present disclosure.

Referring to FIG. 4, a DMD 410 using a superpixel method may be employed for a 3D refractive-index measuring apparatus.

An ultra-high speed/high-definition 3D refractive-index measuring apparatus 400 using the DMD 410 may be formed to include a modulation part, an interferometer, and an imaging part. In this configuration, the DMD 410 may use a superpixel method.

The modulation part may use a wavefront shaper to modify at least one of an illumination angle and a wavefront pattern of an incident ray which is led to a sample. The modulation part may modify an illumination angle of an incident angle, which is led to a sample, through the DMD 410.

The modulation part may include a DMD 410, a first lens 431, a second lens 432, a spatial filter 420, and a plurality of lenses 441 and 442. The plurality of lenses 441 and 442 may be used with, e.g., a tube lens and a condenser lens, respectively.

The DMD 410, as a wavefront shaper, may include an array including a multiplicity of micromirrors.

The first lens 431 and the second lens 432 may transmit a 2D optical field which is reflected from the DMD 410. The first lens 431 and the second lens 432 may be arranged with at least one or more centers which stray from the optical axis by specific intervals.

The spatial filter 420 may be interposed between the first lens 431 and the second lens 432 and may thereby control a phase of a first diffracted ray to adjust a plane-wave advancing angle of an incident ray having a linear gradient.

The plurality of lenses 441 and 442 may enlarge a plane-wave advancing angle of an incident ray which is led to a sample.

In the modulation part, a multiplicity of pixels of the DMD 410 may be grouped to compose a superpixel, and may be treated as to such a degree that the pixels are hardly distinctive due to a scaling-down to a diffraction limit. Then, a superpixel array may be formed to have a phase adjustable in the range of 0~2π and may be adjusted in phase to control a plane-wave advancing angle of an incident ray having a linear phase gradient.

On the other hand, there has been disclosed an optical phase modulation method using a superpixel, in which pixels of the DMD 410 are grouped, by A. Mosk [Non-patent document 5]. This method is to differently represent phases of rays according to positions of micromirrors by aligning lenses, which transmit an optical field reflected from the DMD 410, to slightly stray from the optical axis. Accordingly, if pixels of a superpixel are treated as being indistinct through a scaling-down to a diffraction limit in the configuration that the spatial filter 420 is interposed between the lenses 431 and 432, it may be permissible to complete a superpixel array whose phase is controllable in the range 0~2π. This method may be employed to allow a linear phase gradient and to represent a plane wave which advances in a desired angle. As also, since this method is inevitable to have a limit to a representable phase gradient because of a superpixel size, it may be allowable to use two lenses, which enlarge a representing angle of an incident ray and apply the enlarged incident ray to a sample, for 3D optical tomography.

The interferometer may measure a 2D optical field, which passes through a sample, along at least one or more incident rays.

The imaging part may obtain 3D refractive-index tomograms through information of the measured 2D optical field.

With respect to an operating sequence along an advancing course of a ray, a ray emitted from a light source, like a laser, may be controlled with phase through a wavefront shaper. The light source may include a light source of visible frequency light range.

A wavefront shaper may be used to modify at least one of an illumination angle and a wavefront pattern of an incident ray which is led to a sample. The wavefront shaper may be used with the DMD 410 including an array with a multiplicity of micromirrors. At least one or more centers of the first lens 431 and the second lens 432 may be aligned to stray from the optical axis by a specific interval. And, the spatial filter 420 may be interposed between the first lens 431 and the second lens 432, and may be scaled down to a diffraction limit. Then, pixels of the DMD 410, which are grouped to compose a superpixel, may be treated as being indistinct to form an superpixel array whose phase is controllable in the range 0~2π. For this configuration, the first lens 431 and the second lens 432 may be employed to build a 4-f imaging system and the image scaling-down magnification may be properly set by focal lengths of the first lens 431 and the second lens 432. Thereby, a superpixel formed of the DMD 410 may be scaled down to allow a configuration with a half wavelength which reaches a diffraction limit of an incident ray. Then, a phase of the superpixel array may be adjusted to control a plane-wave advancing angle of an incident ray having a linear phase gradient and the controlled plane-wave advancing angle may be enlarged through the plurality of lenses 441 and 442 to lead the enlarged incident ray to a sample.

A 2D optical field passing through a sample may be measured by the interferometer along at least one or more incident rays. Then, it may be allowable to obtain 3D refractive-index tomograms through information of the measured 2D optical field.

Consequently, for ultra-high speed optical tomography, it may be allowable to measure 3D refractive-index tomograms in high speed and precision by using the DMD 410 to have incident rays different in angles each other and to control the incident rays in stability and high speed.

Figure 5:
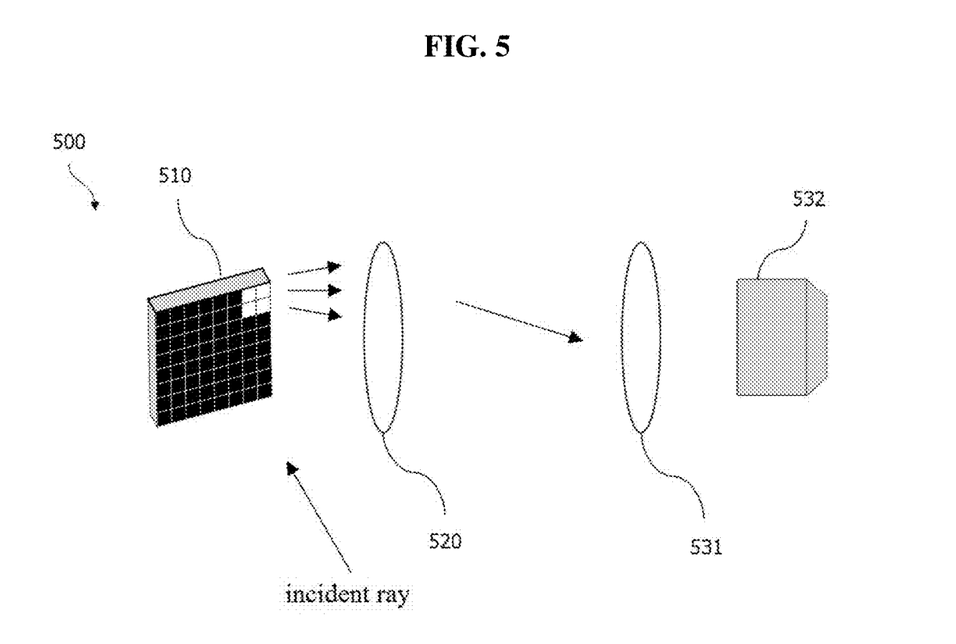
FIG. 5 is a diagram illustrating an ultra-high speed/high-precision 3D refractive-index measuring apparatus using a digital micromirror device according to still another embodiment of the present disclosure.

FIG. 5 is a diagram illustrating an ultra-high speed/high-precision 3D refractive-index measuring apparatus using a digital micromirror device (DMD) according to still another embodiment of the present disclosure.

Referring to FIG. 5, a DMD 510 may be used as an individual source controllable laser array.

An ultra-high-speed/high-definition 3D refractive-index measuring apparatus 500 using the DMD 410 may be formed to include a modulation part, an interferometer, and an imaging part. In this configuration, the DMD 510 may be used as an individual source controllable laser array.

The modulation part may use a wavefront shaper to modify at least one of an illumination angle and a wavefront pattern of an incident ray which is led to a sample. The modulation part may modify an illumination angle of an incident angle, which is led to a sample, through the DMD 510.

The modulation part may include the DMD 510, a first lens 520, and a plurality of lenses 531 and 532.

The DMD 510, as a wavefront shaper, may be equipped with an array including a multiplicity of micromirrors.

The first lens 520 may transmit a 2D optical field which is reflected from the DMD 510.

The plurality of lenses 531 and 532 may enlarge a plane-wave advancing angle of an incident ray and may lead the enlarged incident ray to a sample. The pluralities of lenses 531 and 532 may be used, e.g., with a tube lens and a condenser lens.

The modulation part may form a laser array, which is controllable with individual light sources in positions of a multiplicity of micromirrors, by placing the DMD 510 on an optically aligned Fourier plane, and may control a plane-wave advancing angle of an incident ray by changing positions of the multiplicity of micromirrors which reflects the incident ray. For this function, a plane wave may be illuminated to the DMD 510 which is placed on a Fourier plane and only specific micromirrors may be activated to reflect their corresponding rays. Then, a ray led to a sample may be generated with a specific spatial frequency, i.e., a plane wave may be generated with a specific incident angle.

The interferometer may measure a 2D optical field, which passes through a sample, along at least one or more incident rays.

The imaging part may obtain 3D refractive-index tomograms through information of the measured 2D optical field.

Summarily, an incident ray led to a sample may be controlled in angle by placing the DMD 510 on an optically aligned Fourier plane of the system and by changing positions of the micromirrors which reflect the incident ray. During this, it may be permissible to properly adjust modifications of the lenses for dimensional correspondence between a numerical aperture of the condenser lens and the DMD 510.

With respect to an operating sequence along an advancing course of a ray, a ray emitted from a light source, like a laser, may be controlled with phase through a wavefront shaper. The light source may include a light source of visible frequency light range.

A wavefront shaper may be used to modify at least one of an illumination angle and a wavefront pattern of an incident ray which is led to a sample.

Hereby, it may be permissible to form a laser array, which is controllable with positions of a multiplicity of micromirrors through individual light sources, by using the DMD 510 with an array of a multiplicity of micromirrors as a wavefront and by placing the DMD 510 on an optically aligned Fourier plane. Then, the positions of the multiplicity of micromirrors reflecting an incident ray may be changed through a laser array to control a plane-wave advancing angle of the incident ray. The controlled plane-wave advancing angle may be enlarged through the plurality of lenses 531 and 532 and the enlarged incident ray may be led to a sample.

A 2D optical field passing through a sample may be measured by the interferometer along at least one or more incident rays. Then, it may be allowable to obtain 3D refractive-index tomograms through information of the measured 2D optical field.

Consequently, for ultra-high speed optical tomography, it may be allowable to measure 3D refractive-index tomograms in high speed and precision by using the DMD 510 as an individual source controllable laser array to have incident rays different in angles each other and to control the incident rays in stability and high speed.

Figure 6:
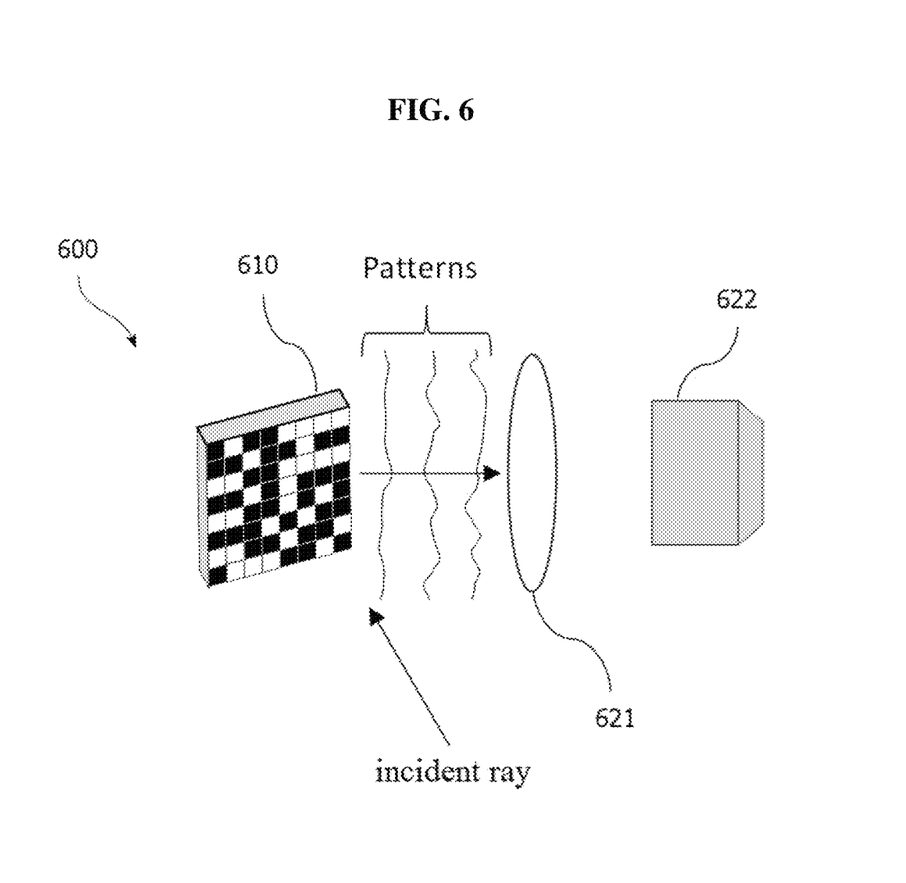
FIG. 6 is a diagram illustrating an ultra-high speed/high-precision 3D refractive-index measuring apparatus using a digital micromirror device according to still another embodiment of the present disclosure.

FIG. 6 is a diagram illustrating an ultra-high-speed/high-precision 3D refractive-index measuring apparatus using a digital micromirror device (DMD) according to still another embodiment of the present disclosure.

Referring to FIG. 6, a DMD 610 may be used as an illumination pattern controller.

An ultra-high-speed/high-definition 3D refractive-index measuring apparatus 600 using DMD may be formed to include a DMD 610, a first lens 612, a second lens 622, an interferometer, and an imaging part. In this configuration, the DMD 610 may be used as an illumination pattern controller.

With the DMD 610, the ultra-high speed/high-definition 3D refractive-index measuring apparatus 600 using a wavefront shaper may lead at least one or more incident ray patterns to a sample.

The first lens 621 and the second lens 622 may enlarge a plane-wave advancing angle of an incident ray which is led to a sample.

The interferometer may modify an incident ray in pattern and may measure a 2D optical field for at least one or more incident ray patterns.

The imaging part may obtain 3D refractive-index tomograms by numerically analyzing a reaction of a sample to differently angled plane waves, which are included in the incident ray patterns, from information of a 2D optical field.

Summarily, the ultra-high speed/high-precision 3D refractive-index measuring apparatus 600 may image an incident ray pattern of the DMD 610 on a plane of a sample, may change the incident ray pattern, and may obtain a reaction of the sample to differently angled plane waves, which are included in the pattern, from optical field information measured by taking an image of a 2D optical field. For example, by modifying an incident ray pattern, it may be allowable to change a phase of a plane wave because the pattern includes the phase of the plane wave. This functionality may be accomplishable by providing information of a known pattern in addition to structured illumination information and by numerically analyzing a reaction of a sample to an incident ray which accords to variation of each phase of plane waves.

Based on a multiplicity of 2D optical field measured through the aforementioned mechanism, it may be permissible to a 3D refractive-index distribution profile through 3D optical diffraction tomography.

With respect to an operating sequence along an advancing course of a ray, a ray emitted from a light source, like a laser, may be controlled with phase through a wavefront shaper. The light source may include a light source of visible frequency light range.

The DMD 610 may be used to lead at least one or more incident ray patterns to the surface of a sample. Then, a 2D optical field to at least one or more incident ray patterns may be measured through the interferometer by changing the incident ray in pattern. And it may be allowable to obtain 3D refractive-index tomograms by numerically analyzing a reaction of a sample to differently angled plane waves, which are included in the incident ray patterns, from information of a 2D optical field.

Consequently, for ultra-high speed optical tomography, it may be allowable to measure 3D refractive-index tomograms in high speed and precision by using the DMD 610 as an illumination pattern controller to have incident rays different in patterns to each other and to control the incident rays in stability and high speed.

As described in conjunction with FIGS. 1 to 6, a DM or a DMD may be used to control an incident ray and thereafter to lead the controlled incident ray to a sample. As a 2D optical field passing through the sample is measured along a variety of incident rays and the measured information of the 2D optical field may be processed in a 3D optical diffraction tomography algorithm, it may be allowable to obtain 3D scattering potentials or 3D refractive-index tomograms.

A general interferometer may be employed in measuring a 2D optical field. For example, a 2D optical field measuring method may be performed with temporal/spatial intensity modulation accompanying Mach-Zehnder interferometer, phase shifting interferometer, quantitative phase imaging unit, and so on [Non-patent document 6].

While embodiments of the present disclosure have been shown and described with reference to the accompanying drawings thereof, it will be understood by those skilled in the art that various changes and modifications in form and details may be made therein without departing from the spirit and scope of the present disclosure as defined by the appended claims and their equivalents. For example, it may be allowable to achieve desired results although the embodiments of the present disclosure are preformed in other sequences different from the descriptions, and/or the elements, such as system, structure, device, circuit, and so on, are combined or assembled in other ways different from the descriptions, replaced or substituted with other elements or their equivalents.

Therefore, other implementations, other embodiments, and equivalents of the appended claims may be included in the scope of the appended claims.

What is claimed is:

1. A method for measuring three-dimensional (3D) refractive-index tomograms using a wavefront shaper in ultra-high speed and high precision, the method comprising:
    leading a first incident ray pattern to a portion of a surface of a sample using a digital micromirror device (DMD), the first incident ray pattern including first angled plane waves having a first angle;
    measuring a first two-dimensional (2D) optical field to the first incident ray pattern through an interferometer;
    leading a second incident ray pattern to only the same portion of the surface of the sample as the first incident ray pattern using the DMD without the second incident ray pattern being led to another distinct portion of the surface of the sample, the second incident ray pattern having a ray pattern that is distinct from a ray pattern of the first incident ray pattern, and the second incident ray pattern including second angled plane waves having a second angle that is distinct from the first angle of the first angled plane waves of the first incident ray pattern;
    measuring a second 2D optical field to the second incident ray pattern through the interferometer;
    numerically analyzing a reaction of the same portion of the surface of the sample to the first angled plane waves and the second angled plane waves that are respectively included in the first incident ray pattern and the second incident ray pattern from the measured first 2D optical field and the measured second 2D optical field; and
    obtaining 3D refractive-index tomograms based on the numerical analysis.

2. An apparatus for measuring three-dimensional (3D) refractive-index tomograms using a wavefront shaper in ultra-high speed and high precision, the apparatus comprising:
    a digital micromirror device (DMD) configured to lead a first incident ray pattern including first angled plane waves having a first angle to a portion of a surface of a sample and a second incident ray pattern including second angled plane waves having a second angle that is distinct from the first angle of the first angled plane waves of the first incident ray pattern to only the same portion of the surface of the sample as the first incident ray pattern, the second incident ray pattern having a ray pattern that is distinct from a ray pattern of the first incident ray pattern;
    a first lens and a second lens that enlarge a plane-wave advancing angle of the first incident ray pattern and the second incident ray pattern and lead the enlarged first incident ray pattern and the enlarged second ray incident pattern to the sample;
    an interferometer configured to measure a first two-dimensional (2D) optical field to the enlarged first incident ray pattern and measure a second 2D optical field to the enlarged second incident ray pattern; and
    wherein a reaction of the same portion of the surface of the sample to the first angled plane waves and the second angled plane waves that are respectively included in the enlarged first incident ray pattern and the enlarged second incident ray pattern from the measured first 2D optical field and the measured second 2D optical field is numerically analyzed to obtain 3D refractive-index tomograms.

* * * * *